United States Patent [19]

Kalvoda

[11] 4,285,937
[45] Aug. 25, 1981

[54] NOVEL ANDROSTADIENE-17-CARBOXYLIC ACID ESTERS

[75] Inventor: Jaroslav Kalvoda, Binningen, Switzerland

[73] Assignee: Ciba-Geigy Corporation, Ardsley, N.Y.

[21] Appl. No.: 89,677

[22] Filed: Oct. 30, 1979

Related U.S. Application Data

[63] Continuation-in-part of Ser. No. 936,285, Aug. 23, 1978, abandoned, which is a continuation of Ser. No. 770,155, Feb. 18, 1977, abandoned.

[30] Foreign Application Priority Data

Feb. 24, 1976 [CH] Switzerland .................. 2253/76

[51] Int. Cl.³ .................. C07J 3/00; A61K 31/56
[52] U.S. Cl. .................. 424/243; 260/397.1; 260/397.45; 260/239.55 R
[58] Field of Search .................. 260/397.1; 424/243

[56] References Cited

U.S. PATENT DOCUMENTS

| | | | |
|---|---|---|---|
| 3,636,010 | 1/1972 | Anner et al. | 260/397.1 |
| 3,856,828 | 12/1974 | Phillipps et al. | 260/397.1 |
| 4,093,721 | 6/1978 | Phillipps et al. | 260/397.1 |

OTHER PUBLICATIONS

"Steroid Drugs" by Applezweig, (1962), pp. 523 and 524.

*Primary Examiner*—Elbert L. Roberts
*Attorney, Agent, or Firm*—Norbert Gruenfeld; Prabodh I. Almaula

[57] ABSTRACT

The invention provides novel esters of androstadiene 17-carboxyclic acids of the formula

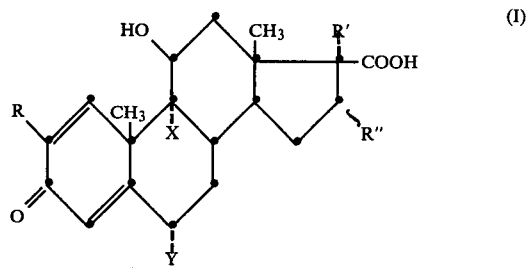

wherein R' represents a hydroxyl group which is esterified with a carboxyclic acid having not more than 7 carbon atoms, R" represents a methyl group in the α- or β-position or the methylene group, wherein R is H or Cl, each of X and Y represents a hydrogen, chlorine or fluorine atom, with the proviso that at least one of these substituents is one of these halogens, when R is Cl, and that Y is only Cl or F and X only Cl, when R is H and that the androstadiene-17-carboxylic acid ester group does not contain more than 11 carbon atoms.

The new esters have pronounced antiinflammatory action coupled with remarkably low systemic side effects on thymus, adrenals and body weight. They are especially suitable to be used in dermatology.

16 Claims, No Drawings

NOVEL ANDROSTADIENE-17-CARBOXYLIC ACID ESTERS

This is a continuation in part of patent application Ser. No. 936,285 filed Aug. 23, 1978, which is, in turn, a continuation application of patent application Ser. No. 770,155 filed Feb. 18, 1977 (both of which are now abandoned).

The invention relates to novel esters of androstadiene-17-carboxylic acids of the formula

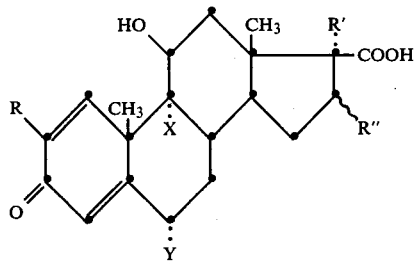

wherein R' represents a hydroxyl group which is esterified with a carboxylic acid having not more than 7 carbon atoms, R" represents a methyl group in the α- or β-position or the methylene group, wherein R is H or Cl, each of X and Y represents a hydrogen, chlorine or fluorine atom, with the proviso that at least one of these substituents is one of said halogens when R is Cl, and that Y is only Cl or F and X only Cl, when R is H and that the androstadiene-17-carboxylic acid ester group does not contain more than 11 carbon atoms, as well as a process for the manufacture thereof and also to pharmaceutical preparations which contain these compounds and to their use, preferably in the form of pharmaceutical preparations.

The above mentioned esters of the steroid-17-carboxylic acids are derived from alcohols containing 1 to 10 carbon atoms of the aliphatic, araliphatic or heterocyclic series which are unsubstituted or substituted by halogen, hydroxyl, alkoxy or acyloxy and are in particular lower aliphatic alcohols containing 1 to 5 carbon atoms which are unsubstituted or substituted by chlorine, fluorine, bromine, hydroxyl, lower alkoxy or lower alkanoyloxy, such as methyl alcohol, ethyl alcohol, propyl alcohol, isopropyl alcohol, the butyl or amyl alcohols, and araliphatic alcohols, such as benzyl alcohol or phenethyl alcohol or the derivatives thereof which are substituted in the aromatic nucleus and/or in the aliphatic moiety by the aforementioned groups, or heterocyclic alcohols, such as tetrahydrofuranol or tetrahydropyranol. Substituted alcohols to be singled out for special mention are those which are substituted by a hydroxyl group, that is to say, for example, divalent and trivalent alcohols, such as ethylene glycol or propylene glycol and glycerol and their O-mono-lower alkyl or O-mono-lower alkanoyloxy derivatives. The term "lower" used throughout this specification in connection with the number of carbon atoms of organic groups denotes groups having 1to 7 carbon atoms, unless otherwise expressly defined. Examples of substituted alcohols are the lower aliphatic halohydrins, for example ethylene chlorohydrin or ethylene fluorohydrin. However, the 17-ester group can also be the fluoromethoxycarbonyl, chloromethoxycarbonyl or 2-fluoro- or 2-chloroethoxycarbonyl group.

An esterified hydroxyl group R' is derived from a saturated or unsaturated carboxylic acid of 1 to 7 carbon atoms which is unsubstituted or substituted by halogen atoms, hydroxyl or lower alkoxy groups and is for example the formyloxy, acetoxy, propionyloxy, butyryloxy, valeryloxy, diethylacetoxy, caproyloxy, chloroacetoxy, chloropropionyloxy, oxypropionyloxy or acetoxypropionyloxy group.

The above esters of the compounds of the formula (I) possess valuable pharmacological properties. For example, they have in particular a pronounced antiinflammatory action, as can be demonstrated in animal tests, for example on rats in the foreign body granuloma test. When applied locally in the dosage range between 0.001 mg per cotton wool pellet and 0.03 mg per cotton wool pellet they exhibit a marked antiinflammatory action. An action on the thymus, adrenals and body weight is observed in this mode of administration only at doses over 0.3 mg per cotton wool pellet. The antiinflammatory activity of the new compounds is, moreover, also very pronounced in the rat-ear dermatitis inhibition test according to Tonelli. The novel compounds can therefore be used as antiinflammatory agents, in particular in dermatology. However, they are also valuable intermediates for obtaining other useful substances, especially pharmacologically active compounds.

Novel esters to be mentioned as particularly highly active compounds are in particular the methyl esters of 2-chloro-6α,9α-difluoro-11β-hydroxy-17α-propionyloxy-16α-methyl-3,20-dioxo-androsta-1,4-diene-17-carboxylic acid, of 2,9α-dichloro-6α-fluoro-11β-hydroxy-17α-propionyloxy-16α-methyl-3,20-dioxo-androsta-1,4-diene 17-carboxylic acid and of 9α-chloro-6α-fluoro-11β-hydroxy-17α-propionyloxy-16α-methyl-3,20-dioxo-antrosta-1,4-diene 17-carboxylic acid.

The novel steroid-17-carboxylic acid esters of the present invention can be prepared in a manner which is known per se. In particular, they can be obtained by (a) converting a carboxylic acid of the formula (I) or a salt thereof, or a functional derivative thereof which can be converted into an ester, into the carboxylic acid ester, or (b) esterifying the 17α-hydroxyl group in an ester of a carboxylic acid of the formula (I), wherein R' represents a free hydroxyl group and R" represents a methyl or methylene group, while optionally protecting the 11-hydroxyl group temporarily, or (c) the addition of chlorine to the 1,2-double bond in an ester of a carboxylic acid of the formula (I) wherein R is hydrogen and R' and R" are as defined in formula (I), and each of X and Y represents a hydrogen, chlorine or fluorine atom with the proviso that at least one of these substituents is one of these halogens, while optionally protecting the 11-hydroxyl group temporarily, and dehydrochlorination of the resultant 1,2-dichloro compound or, (d) treating an ester of a carboxylic acid or the formula

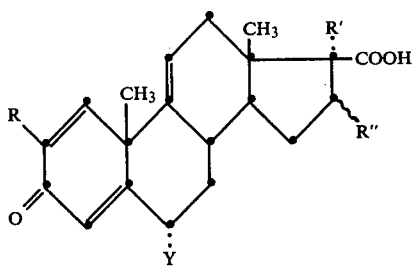

(II)

wherein R, R', R" and Y are as defined in formula (I), with hypochlorous acid or with a hypochlorous acid donor, or (e) treating a 17-ester of a carboxylic acid of the formula

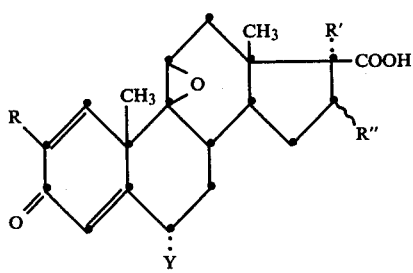

(III)

wherein R, R', R" and Y are as defined in formula (I), with hydrogen chloride or hydrogen fluoride or with agents which yield these acids, and, if desired, in resultant esters of the steroid-17-carboxylic acids in which the hydrocarbon radical of the ester group contains halogen, hydroxyl, alkoxy or acyloxy substituents, optionally converting these groups into one another.

The esterification of the steroid-17-carboxylic acids in accordance with (a) can be carried out in a manner which is known per se. For example, the free acid is reacted with a reactive functional derivative of the respective alcohol, such as an alkyl halide, for example an alkyl bromide or alkyl chloride, or a dialkyl sulphate, such as dimethyl sulphate, in the presence of a base, such as pyridine or sodium hydroxide solution, or the reaction is performed direct with the alcohol, with the addition of a dehydrating agent, such as sulphuric acid or hydrogen chloride or zinc chloride. The simple alkyl esters, such as in particular the methyl ester, can be obtained by reacting in a manner known per se the acids with the respective diazoalkane, for example diazomethane, preferably in an ether and at temperatures between $-5°$ and $+30°$ C., or with the respective S-alkyl-N,N'-dicyclohexyliso-thioura, preferably in an aprotic agent and at temperatures between 25° and 100° C.

If metal salts of the above acids are used as starting materials, in particular alkali metal salts, then the esters are obtained by reaction with the halogenated hydrocarbon suitable for introducing the hydrocarbon radical, such as an alkyl halide, for example methyl bromide, ethyl chloride or benzyl chloride or a dialkyl sulphate, such as dimethyl sulphate, in a manner known per se. The reaction is preferably carried out in a polar medium, for example acetone, methyl ethyl ketone or dimethyl formamide, preferably at temperatures between 25° and 100° C.

The esters can also be obtained from functional derivatives of the 17-steroid-carboxylic acids of the formula (I), for example from the halides, by reaction with the respective alcohol or from other esters by transesterification.

The conversion of a free hydroxyl group in the 17α-position in accordance with (b) into an esterified hydroxyl group is effected in a manner known per se by reaction with the respective acid or a functional derivative, such as a halide or the anhydride, advantageously in the presence of an acid catalyst, for example p-toluenesulphonic acid, perchloric acid, or with an acid ion exchanger, such as Amberlite IR120, or sulphosalicyclic acid and, with particular advantage, in the presence of trifluoroacetic anhydride. The reaction is advantageously carried out in a chlorinated hydrocarbon, such as benzene or toluene, or in a chlorinated aliphatic hydrocarbon, such as methylene chloride or chloroform, or an excess of the acid itself is used as solvent. The reactions are advantageously carried out in the temperature range between 20° and 100° C. When using acid halides, the esterification can also be carried out in the presence of a base, such as pyridine.

If desired, the 11β-hydroxyl group can be protected temporarily during the esterification of a 7α-hydroxyl group, for example in accordance with the process described above. The esterification with trifluoracetic acid can be employed for this purpose. The trifluoroacetates are obtained by reacting the starting materials with trifluoroacetic chloride or anhydride in a manner known per se. It is known that this ester group can be easily split off again by hydrolysis or solvolysis, for example by treatment with hydroxides, carbonates, bicarbonates or acetates of alkali metals or alkaline earth metals, for example in alcoholic or aqueous-alcoholic solution, for example in methanolic solution, or with alcohols alone. A particular method of carrying out the solvolysis of the 11β-trifluoroacetate group is that described in German patent specification No. 1,593,519. This method comprises treating the 11-ester in a lower alcohol with a salt of an acid whose pK value is in the range between about 2.3 and about 7.3, such as sodium or potassium azide or sodium or potassium formiate. If appropriate, this salt can also only be used in catalytic amounts. Furthermore, the hydrolysis of the 11-trifluoroacetate group can also be effected by treatment with other basic reagents, for example with amines, in particular heterocyclic bases, such as pyridine or collidine. Finally, the saponification by treatment with silica gel according to the process described in DT-OS No. 2,144,405 is also possible.

According to method (c), the 2-chlorine atom is introduced into esters or steroid-17-carboxylic acids of the formula (I) which do not contain this substituent. This is accomplished by the addition of chlorine to the 1,2-double bond in a manner known per se and dehydrochlorination of the resultant 1,2-dichloro-compound also in a manner known per se.

Preferably elementary chlorine is used for the addition of chlorine and the chlorination is carried out in an inert solvent, for example an ether, such as dioxane or tetrahydrofurane, a halogenated hydrocarbon, for example methylene chloride, or a carboxylic acid, for example a lower aliphatic carboxylic acid, such as acetic acid or propionic acid. Instead of using carboxylic acids it is also possible to use derivatives thereof, such as acid amides, for example dimethyl formamide, or nitriles, such as lower alkylnitriles, for example acetonitrile. Advantageously, mixtures of these solvents can also be used, in particular a mixture of an ether, such as dioxane, with one of the above mentioned lower aliphatic carboxylic acids. The process can be carried out with chlorine in an amount substantially in excess of the theoretical amount; but preferably the stoichiometric amount of chlorine is used. The chlorination is advantageously carried out at low temperature, approx. between $-50°$ and $+30°$ C., for example between $-20°$ and $+10°$ C., and in the dark. The reaction time is normally several hours or days, for example up to 7 days. In a particularly preferred embodiment of the process, the starting steroid is dissolved in one of the solvents mentioned above, for example dioxane, and treated with a solution of the chlorinating agent, for example chlorine, in a lower aliphatic carboxylic acid, for example propionic acid, and this solution is then allowed to stand at the given temperature for several days.

However, the chlorination of the 1,2-double bond can also be effected with mixtures of two different chlorine-containing compounds one of which yields positive and the other negative chlorine. Examples of suitable reagents which are able to set free positive chlorine are chlorinated acid amides or acid imides, such as chlorosuccinimide or chloroacetamide, and reagents which yield negative chlorine are, for example, hydrogen chloride and alkali metal chlorides. The above mentioned solvents can also be used for the addition of chlorine with these reagents.

If desired, the $11\beta$-hydroxyl group can be protected before the chlorination. This can be effected as described above in connection with the esterification of a $17\alpha$-hydroxyl group. The 11-hydroxyl protective group can be removed immediately after the addition of chlorine to the 1,2-double bond or, if appropriate, simultaneously with dehydrochlorination by treatment with a base to be carried out, according to the process, after the chlorination. However, if desired, it is possible not to remove the protective group until after the dehydrochlorination by treatment with a base.

The dehydrochlorination of the 1,2-dichloro compounds obtained by the addition of chlorine to the 1,2-double bond can advantageously be carried out with a base. Suitable bases are, for example, tertiary organic nitrogen bases, such as the lower aliphatic amines, for example triethylamine, or heterocyclic bases, such as pyridine and honologues thereof, for example collidine, or aromatic bases, such as N,N-dialkylaniline. However, it is also possible to use inorganic bases, such as in particular the alkali metal and alkaline earth metal salts also used for removing the above mentioned $11\beta$-hydroxyl protective group, for example potassium or sodium acetate or potassium or sodium bicarbonate, in aqueous-alcoholic solution, and the corresponding hydroxides, in which connection care must be taken that no saponification of the 17-ester group takes place. This is possible by keeping the reaction conditions as mild as possible, such as choice of suitable temperature and concentration of the hydrolysing agent. The dehydrohalogenation is preferably carried out in the temperature range between approx. 20° and 100° C. and over the course of half an hour up to approx. 30 hours, depending on whether the reaction is carried out at elevated or low temperature. Preferably, an excess of the dehydrohalogenating agent is used.

According to method (d), the elements of hypochlorous acid are added in a manner known per se to the 9,11-double bond of esters of carboxylic acids of the formula (II) by, for example, treatment with aqueous hypochlorous acid or with hypochlorous acid donors, such as N-chlorocarboxamides or N-chlorocarboximides (cf. U.S. Pat. No. 3,057,886), in the presence of water and/or an inert solvent, such as a tertiary alcohol, for example butanol, an ether, for example diethyl ether, methyl isopropyl ether, dioxane, or a ketone, such as acetone, optionally in the presence of a strong acid. An advantageous method of carrying out this process is the reaction with tert.-butyl-hypochlorite in an inert water-immiscible solvent, for example a nitro-substituted hydrocarbon, in the presence of perchloric acid (cf. German patent specification No. 2,011,599).

According to method (e), the $9\beta,11\beta$-oxido group in esters of 17-carboxylic acids of the formula (III) are treated in a manner known per se with hydrogen chloride or hydrogen fluoride, or with those agents which are capable of adding these hydrohalic acids to the epoxide to form the corresponding halohydrins. The process can be carried out in aqueous medium or in an inert organic solvent, such as an alcohol or an ether, in particular tetrahydrofurane or dioxane, and also for example diethyl ether or isopropyl ether, a hydrocarbon, such as methylene chloride or chloroform, or an acid amide, such as dimethyl formamide. As compounds which yield hydrogen chloride or hydrogen fluoride it is possible to use the salts of these acids with a tertiary organic base, for example pyridine. A particularly advantageous process is described and claimed in U.S. Pat. No. 3,211,758, in accordance with which the starting product is reacted with an adduct of hydrogen fluoride and urea.

In resultant esters of steroid-17-carboxylic acids which contain halogen atoms, hydroxyl, alkoxy or acyloxy groups as substituents in the alcohol component, these substituents can, if appropriate, be converted into one another in a manner known per se. Thus the hydroxyl group can be replaced by a chlorine atom via a sulphonic acid ester, for example the mesylate or tosylate, by reaction with lithium chloride in acetone, dimethyl formamide or an alcohol. However, the hydroxyl group can also be esterified in known manner with a carboxylic acid, so that steroid-17-carboxylic acid are obtained in which the alcohol component represents a hydrocarbon which is substituted by an acyloxy group.

The starting materials necessary for carrying out the above process are novel and can be prepared in a manner known per se.

Steroid-17-carboxylic acids of the formulae (I), (II) and (III), wherein R' represents a free hydroxyl group, can be obtained in a manner known per se, for example by the side-chain degradation of corresponding 21-hydroxy-pregna-1,4-dien-20-ones with periodic acid. The degradation to the 7-carboxylic acids of 21-hydroxy-pregna-1,4-dien-20-ones with the substituents or double bonds indicated for formula (I), (II) or (III), and wherein R' represents an esterified hydroxyl group, can also be effected with sodium bismuthate, for example in the presence of acetic acid. In resultant steroid-17-carboxylic acids, in which R' represents a free hydroxyl group, this latter can, if desired, be esterified in the manner described above for process variant (b), and in those in which the group R' is present as protected hydroxyl group, this latter can, if desired, be converted into a free hydroxyl group.

The salts of the steroid-17-carboxylic acids are prepared by treating for example a solution or a suspension of the acid in water, or in a mixture of water and an alcohol, with the calculated amount of the respective base, for example an alkali metal hydroxide, or with a carbonate or bicarbonate, and isolating the salt in a manner known per se, for example by precipitation with a suitable solvent or by crystallisation during the concentration of the resultant salt solution, or by lyophilisation.

17α-Esters can also be prepared from 17α-hydroxysteroid-17β-carboxylic acids, for example from those of the formula (I), by reacting them initially with the anhydride corresponding to the ester group to be introduced, whereupon the 17-ester of the mixed anhydride of the respective acid and the steroid-17-carboxylic acid are formed. The reaction is preferably carried out at elevated temperature. The mixed anhydride can be split by solvolysis, for example by treatment with basic or alkaline media, for example with aqueous acetic acid or aqueous pyridine or diethylamine in acetone.

The functional derivatives of the steroid-17-carboxylic acids which can, if desired, be used as starting materials, are prepared in a manner known per se, for example the chloride by reaction with thionyl chloride, sulphuryl chloride or phosphorous tri- or pentachloride.

The invention also relates to those embodiments of the process in which a compound obtainable in any stage of the process is used as starting material and the missing steps are carried out, or the process is interrupted at any stage, or in which a starting material is formed under the reaction conditions.

The present invention also provides pharmaceutical preparations with an ester of an androstadiene-17-carboxylic acid of the formula (I) or a salt of such a compound with salt-forming properties, and a process for the manufacture of such pharmaceutical preparations.

Suitable pharmaceutical preparations are primarily ones for topical application, such as creams, ointments, pastes, foams, tinctures and solutions, which contain approx. 0.02% to approx. 0.1% of active compound, and also preparations for oral administration, for example tablets, coated tablets and capsules, and those for parenteral administration.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool wax or bees-wax, and/or hydrocarbons, for example petroleum jelly (petrolatum) or paraffin oil. Suitable emulsifiers are surface-active substance with primarily hydrophilic properties, such as corresponding non-ionic emulsifiers, for example fatty acid esters of polyalcohols or ethylene oxide adducts thereof, such as polyglycerol fatty acid esters or polyoxyäthylene sorbitan fatty acid esters (Tweens); polyoxyethylene fatty alcohol ethers or esters, or corresponding ionic emulsifiers, such as alkali metal salts of fatty alcohol sulphates, for example sodium lauryl sulphate, sodium cetyl sulphate or sodium stearyl sulphate, which are suctomarily used in the presence of fatty alcohol, for example cetyl alcohol or stearyl alcohol. Additives to the water phase include agents which reduce water loss through evaporation, for example polyalcohols, such as glycerol, sorbitol, propylene glycol and/or polyethylene glycols, as well as preservatives, perfumes etc.

Ointments are water-in-oil emulsions which contain up to 70%, preferably however approx. 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluorolower alkanes, for example dichlorodifluoromethane and dichlorotetrafluoroethane being used as propellants. For the oleaginous phase there are used, inter alia, hydrocarbons, for example paraffin oil, fatty alcohols, for example cetyl alcohol, fatty acid ester, for example isopropyl myristate, and/or other waxes. As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restoring substances, such as fatty acid esters with lower polyethylene glycols, i.e. lipophilic substances which are soluble in the aqueous mixture as substitute for fatty substances which are taken from the skin with the ethanol, and, if necessary, other assistants and additives.

The pharmaceutical preparations for topical application are obtained in known manner, for example by dissolving or suspending the active substance in the base or in a part thereof, if necessary. When processing the active substance in the form or a solution, it is usually dissolved in one of the two phases before the emulsification, and when processing the active substance in the form of a suspension, it is mixed with a part of the base before the emulsification and then added to the remainder of the formulation.

Besides the pharmaceutical preparations which can be applied topically, other suitable preparations are those for enteral, for example oral, and parenteral administration to warm-blooded animals and which contain the pharmacologically active substance as sole ingredient or together with a pharmaceutically acceptable carrier. These pharmaceutical preparations contain about 0.01% to about 10% of active substance and are in dosage unit form, such as coated tablets, capsules, suppositories or ampoules. They are obtained in known manner, for example by conventional mixing, granulating, coating, dissolving or lyophilising methods.

The dosage of active substance depends on the species of warm-blooded animal, the age, and the individual condition as well as on the mode of application.

The present invention also relates to the use of the novel esters of carboxylic acids of the formula (I) and of the salts of such compounds with salt-forming properties, preferably for treating inflammations, chiefly as antiinflammatory glucocorticoids for local application, normally in the form of pharmaceutical preparations, especially in the form of pharmaceutical preparations for topical application.

The novel esters of carboxylic acids of the formula (I) of the present invention can also be used as additives to animal feeds.

The following Examples describe the invention in more detail.

EXAMPLE 1

133 mg of p-toluenesulphonic acid monohydrate are added to a solution, which is stirred at room temperature, of 1.33 g of methyl 2-chloro-6α,9α-difluoro-11β,17α-dihydroxy-16α-methyl-3-oxo-androsta-1,4-diene-17-carboxylate in 40 ml of propionic acid and 5.35 ml of trifluoroacetic anhydride. The reaction solution is stirred for 7 hours at 35° C. and poured into 500 ml of ice/water. The precipitated substance is taken up in chloroform and washed neutral with water. The organic solution is dried over sodium sulphate and concentrated in a water jet vacuum to yield a crystalline crude product from which pure methyl 2-chloro-6α,9α-difluoro-11β-hydroxy-17α-propionyloxy-16α-methyl-3-oxo-androsta-1,4-diene-17-carboxylate is obtained by preparative thin-layer chromatography [eluant: toluene/ethyl acetate (65:35)]. Melting point: 255°–256° C. after crystallisation from methylene chloride/methanol/ether.

The methyl 2-chloro-6α,9α-difluoro-11β,17α-dihydroxy-16α-methyl-3-oxo-androsta-1,4-diene-17-carboxylate used as starting material can be prepared, inter alia, as follows:

A solution of 5 g of 2-chloro-6α,9α-difluoro-11β,17α-21-trihydroxy-16α-methyl-pregna-1,4-diene-3,20-dione in 200 ml of dioxane is treated with 12.5 g of periodic acid in 100 ml of water and the reaction mixture is stirred for 1 hour at room temperature. After addition of 150 ml of water, dioxane is evaporated in a water jet vacuum and the precipitate which has formed is taken up in chloroform and washed with ice-cold dilute sodium hydroxide solution. The sodium hydroxide extract is acidified with ice-cold dilute hydrochloric acid and extracted with chloroform. The dried organic phase is concentrated in a water jet vacuum to yield the free 2-chloro-6α,9α-difluoro-11β,17α-dihydroxy-16α-methyl-3-oxo-androsta-1,4-diene-17-carboxylic acid, which is dissolved in 20 ml of methanol and 40 ml of methylene chloride and esterified with an ethereal diazomethane solution. The solvent is evaporated to yield the methyl 2-chloro-6α,9α-difluoro-11β,17α-dihydroxy-16α-methyl-3-oxo-androsta-1,4-diene-17-carboxylate, which melts at 275°–277° C. after recrystallisation from chloroform/methanol/ether.

EXAMPLE 2

2 g of 2-chloro-9α-fluoro-11β-hydroxy-16β-methyl-3-oxo-17α-propionyloxy-androsta-1,4-diene-17-carboxylic acid are dissolved in 10 ml of methanol and 5 ml of methylene chloride and the solution is treated with an excess of ethereal diazomethane solution. The crude product obtained by concentration is chromatographed through a column of 30 times its amount by weight of silica gel with toluene/ethyl acetate (95:5) as eluant to yield pure methyl 2-chloro-9α-fluoro-11β-hydroxy-17α-propionyloxy-16β-methyl-3-oxo-androsta-1,4-diene-17-carboxylate, which melts at 213°–214° C. after recrystallisation from methylene chloride/ether.

The 2-chloro-9α-fluoro-11β-hydroxy-16β-methyl-3-oxo-17α-propionyloxy-androsta-1,4-diene-17-carboxylate can be prepared, inter alia, as follows:

A solution of 2 g of 2-chloro-9α-fluoro-11β,17α-21-trihydroxy-16β-methyl-pregna-1,4-diene-3,20-dione (prepared by chlorination of betamethasone-21-acetate with chlorine in propionic acid, splitting off 1 mole of hydrochloric acid with pyridine and subsequent mild saponification with potassium carbonate) in 80 ml of dioxane is treated with 5 g of periodic acid in 40 ml of water and the reaction mixture is stirred for 1.5 hours at room temperature. After addition of 60 ml of water, the dioxane is evaporated in a water jet vacuum and the precipitated 2-chloro-9α-fluoro-11β,17α-dihydroxy-16β-methyl-3-oxo-androsta-1,4-diene-17-carboxylic acid is filtered off, thoroughly dried, thereafter dissolved in 32 ml of pyridine and the solution is treated at −10° C. with 8 ml of an ice-cold solution consisting of 25 ml of abs. toluene and 1.9 ml of propionyl chloride. The reaction mixture is allowed to stand for 18 hours at −10° C., then poured into 200 ml of ice/water, acidified with dilute hydrochloric acid and extracted with chloroform. The dried organic phase is concentrated in a water jet vacuum to yield the amorphous 2-chloro-9α-fluoro-11β-hydroxy-16β-methyl-3-oxo-17α-propionyloxy-androsta-1,4-diene-17-carboxylic acid, which is subjected direct to the above described methylation.

EXAMPLE 3

5 g of 2,9α-dichloro-6α-fluoro-11β-hydroxy-17α-propionyloxy-16α-methyl-3-oxo-androsta-1,4-diene-17-carboxylic acid are dissolved in 100 ml of methanol and 25 ml of methylene chloride and esterified with an ethereal diazomethane solution. The crude product obtained by concentration is chromatographed through a column of 30 times its amount by weight of silica gel with toluene/ethyl acetate (90:10) as eluant to yield pure methyl 2,9α-dichloro-6α-fluoro-11β-hydroxy-16α-methyl-3-oxo-17α-propionyloxy-androsta-1,4-diene-17-carboxylate, which melts at 269° C. after recrystallisation from methylene chloride/ether. The 2,9α-dichloro-6α-fluoro-11β-hydroxy-16α-methyl-3-oxo-17α-propionyloxy-androsta-1,4-diene-17-carboxylic acid used as starting material can be prepared, inter alia, as follows:

A solution of 5 g of 2,9α-dichloro-6α-fluoro-11β-17α,21-trihydroxy-16α-methyl-pregna-1,4-diene-3,20-dione (which can be obtained for example by chlorinating the corresponding derivative which is not chlorinated in 2-position and dehydrochlorination, e.g. with pyridine, in known manner) in 200 ml of dioxane is treated with a solution of 12.5 g of periodic acid in 100 ml of water and the reaction mixture is stirred for 1.5 hours at room temperature. After addition of 150 ml water, the dioxane is evaporated in a water jet vacuum. The 2,9α-dichloro-6α-fluoro-11β,17α-dihydroxy-16α-methyl-3-oxo-androsta-1,4-diene-17-carboxylic acid, which is filtered off and well dried, is dissolved in 85 ml of pyridine. The solution is treated at −10° C. with 20 ml of an ice-cold solution consisting of 25 ml of abs. toluene and 1.9 ml of propionyl chloride and the mixture is allowed to stand for 18 hours at −10° C. The batch is then poured into 500 ml of ice/water, acidified with dilute hydrochloric acid and extracted with chloroform. The dried organic phase is concentrated in a water jet vacuum to yield the amorphous 2,9α-dichloro-6α-fluoro-11β-hydroxy-16α-methyl-3-oxo-17α-propionyloxy-androsta-1,4-diene-17-carboxylic acid.

EXAMPLE 4

A solution of 4 g of methyl 6α,9α-difluoro-11β-hydroxy-16α-methyl-3-oxo-17α-propionyloxy-androsta-1,4-diene-17-carboxylate in 325 ml of dioxane is treated with 19.5 ml of a 1 M solution of chlorine in propionic acid. The reaction mixture is stirred for 3 days at 4° C., then poured into ice/water and extracted 3 times in the usual way with methylene chloride. The organic solutions are washed in succession with potassium iodide/thiosulphate solution, water, 2 N sodium hydroxide solution and again with water, dried, and concentrated in a water jet vacuum. The crude product is dissolved in 98 ml of pyridine and allowed to stand for 12 hours at room temperature. The solution is then poured into water and extracted once more with methylene chloride. The extracts are washed with ice-cold 2 N sulphuric acid and with water, dried, and concentrated in vacuo. The amorphous reaction product is subsequently purified by chromatography through a column of 50 times its amount by weight of silica gel (eluant: toluene/ethyl acetate (80:20) and, after crystallisation from methylene chloride/ether, yields a sample of the methyl 2-chloro-6α,9α-difluoro-11β-hydroxy-16α-methyl-3-oxo-17α-propionyloxy-androsta-1,4-diene-17-carboxylate which melts at 254°–256° C.

The starting material is prepared for example in known manner by bismuthate degradation of flumethasone-17-propionate and subsequent methylation of the resultant 6α,9α-difluoro-11β-hydroxy-16α-methyl-3-oxo-17α-propionyloxy-androsta-1,4-diene-17-carboxylic acid.

EXAMPLE 5

3.5 g of methyl 2-chloro-6α-fluoro-16α-methyl-3-oxo-17α-propionyloxy-androsta-1,4,9(11)-triene-17-carboxylate are suspended in 70 ml of tert.-butanol and, while introducing nitrogen and with stirring, the suspension is treated successively with 3.5 ml of a 10% solution of perchloric acid and 1 ml of tert.-butylhypochlorite. The reaction mixture is stirred for a further 2 hours at room temperature, then diluted with 50 ml of water and the precipitated solid is filtered off. The filter residue is then washed with methanol/water (1:1) and with pure water, dried, and taken up in chloroform. The solution is dried over sodium sulphate and concentrated in a water jet vacuum to yield 3.2 g of crude product, which is chromatographed through a column of 30 times its amount by weight of silica gel [solvent mixture: toluene/ethyl acetate (90:10)] to yield the pure methyl 2,9α-dichloro-6α-fluoro-11β-hydroxy-16α-methyl-3-oxo-17α-propionyloxy-17-carboxylate. The compound melts at 268°–270° C. after two recrystallisations from methylene chloride/ether (with decomp.).

The triene used as starting material is prepared from paramethasone-17-propionate in a manner known per se by side-chain degradation, methylation, chlorination in 2-position and dehydration in 11-position.

EXAMPLE 6

6.42 g of methyl 6α-fluoro-16α-methyl-3-oxo-17α-propionyloxy-androsta-1,4,9(11)-triene-17-carboxylate are suspended in 128 ml of tert. butanol and, while introducing nitrogen and with stirring, the suspension is treated successively with 6.4 ml of a 10% solution of perchloric acid and 1.8 ml of tert. butylhypochlorite. The reaction mixture is stirred for a further 3 hours at room temperature, then diluted with 50 ml of water, and the precipitated product is filtered off. The filter residue is thereafter washed with methanol/water (1:1) and with pure water, dried, and taken up in chloroform. The solution is dried over sodium sulphate and concentrated in a water jet vacuum to yield 6 g of crude product which is chromatographed through a column of 30 times its weight of silica gel [solvent mixture: toluene/ethyl acetate (90:10)] to yield the methyl 9α-chloro-6α-fluoro-11β-hydroxy-16α-methyl-3-oxo-17α-propionyloxy-androsta-1,4-diene-17-carboxylate which melts at 264°–265° C. after recrystallisation from methylene chloride/ether.

The starting material can be obtained from methyl 6α-fluoro-11β-hydroxy-16α-methyl-3-oxo-17α-propionyloxy-androsta-1,4-diene-17-carboxylate by splitting off water with methane-sulphonyl chloride/sulphur dioxide in dimethyl formamide/collidine. This ester, which melts at 210°–212° C., can be obtained in known manner from paramethasone-17-propionate by bismuthate degradation of the side-chain and subsequent methylation of the 17-carboxyl group.

EXAMPLE 7

An ointment containing 0.1% of Methyl 9α-chloro-6α-fluoro-11β-hydroxy-16α-methyl-3-oxo-17α-propionyloxy-androsta-1,4-diene-17-carboxylate

| Composition | |
|---|---|
| Methyl 9α-chloro-6α-fluoro-11β-hydroxy-16α-methyl-3-oxo-17α-propionyloxy-androsta-1,4-diene-17-carboxylate | 0.1% |
| white petroleum jelly | 45.0% |
| liquid paraffin | 19.6% |
| cetyl alcohol | 5.0% |
| beeswax | 5.0% |
| sorbitane sesquioleate | 5.0% |
| p-hydroxybenzoic acid ester | 0.2% |
| perfume | 0.1% |
| water | 20.0% |

The fatty substances and emulsifiers are melted together. The preservative is dissolved in water and the solution is emulsified into the fatty salt at elevated temperature. After cooling, a suspension of the active compound in a part of the fatty melt is incorporated into the emulsion and the perfume is then added.

EXAMPLE 8

A cream containing 0.1% of Chloromethyl 2,9α-dichloro-6α-fluoro-11β-hydroxy-16α-methyl-3-oxo-17α-propionyloxy-androsta-1,4-diene 17β-carboxylate as the active ingredient is prepared as follows:

A mixture is prepared containing 0.1 g of the above said active ingredient, 12.9 g of white soft paraffin (vaseline) and 10.0 g of emulsifying cetylstearyl alcohol (consisting of 9 part of a mixture of these 2 alcohols and 1 part of a mixture of sodium cetyl sulfate and stearyl sulfate), as well as 10.0 g of oleic acid decyl ester, and this is emulsified in the solution of 1.0 g of 2-phenoxyethanol in 25.0 g of 1,2-propandiol and 41.0 g of water.

I claim:

1. Esters of androstadiene-17-carboxylic acids of the formula

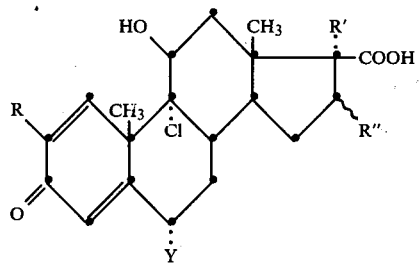

wherein R' represents a hydroxyl group which is esterified with a lower aliphatic carboxylic acid having not more than 7 carbon atoms, R" represents a methyl group in the alpha- or beta-position or the methylene group, R is H or Cl, and Y represents a hydrogen, chlorine or fluorine atom, with the proviso that Y is only Cl or F, when R is H and that the androstadiene-17-carboxylic acid ester group is derived from an aliphatic alcohol, so that said group contains not more than 6 carbon atoms.

2. Compounds according to claim 1, wherein the esters of the steroid-17-carboxylic acids are derived from said aliphatic alcohols which are unsubstituted or substituted by hydroxyl, lower alkoxy or acyloxy.

3. Compounds according to claim 1, wherein the esters of the steroid-17-carboxylic acids are derived from lower aliphatic alcohols having 1 to 5 carbon atoms.

4. Compounds according to claim 1, wherein the esters of the steroid-17-carboxylic acids are derived from dihydric or trihydric alcohols.

5. Compounds according to claim 1, wherein an esterified hydroxyl group R' is the formyloxy, acetoxy, propionyloxy, butyryloxy, valeryloxy, diethylacetoxy or the caproyloxy group.

6. A compound according to claim 1, which is the methyl 2,9α-dichloro-6α-fluoro-11β-hydroxy-16α-methyl-3,20-dioxo-17α-propionyloxy-androsta-1,4-diene-17-carboxylate.

7. The methyl 9alpha-chloro-6alpha-fluoro-11beta-hydroxy-16alpha-methyl-3-oxo-17alpha-propionyloxy-androsta-1,4-diene-17-carboxylate.

8. The methyl 2-chloro-9alpha-fluoro-11beta-hydroxy-17alpha-propionyloxy-16beta-methyl-3-oxo-androsta-1,4-diene-17-carboxylate.

9. A compound according to claim 1, which is the chloromethyl 2,9α-dichloro-6α-fluoro-11β-hydroxy-16α-methyl-3-oxo-17α-propionyloxy-17-androsta-1,4-diene-17β-carboxylate.

10. An antiinflammatory pharmaceutical preparation which contains an antiinflammatory effective amount of a compound according to claim 1, together with a pharmaceutical carrier.

11. Androstadiene-17-carboxylic acids of the formula

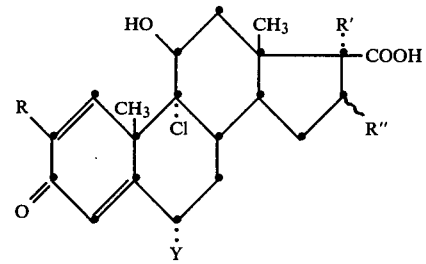

wherein R' represents a free hydroxyl group or a hydroxyl group which is esterified with a lower aliphatic carboxylic acid having not more than 7 carbon atoms, R" represents a methyl group in the alpha- or beta-position or the methylene group, R is H or Cl, and Y represents a hydrogen, chlorine or fluorine atom, with the proviso that Y is only Cl or F, when R is H.

12. Compounds according to claim 1, wherein Y represents fluorine.

13. Compounds according to claim 1, wherein R represents hydrogen.

14. Compounds according to claim 11, wherein R is hydrogen, Y is fluorine and R' is lower alkanoyloxy.

15. Esters of androstadiene-17-carboxylic acids of the formula

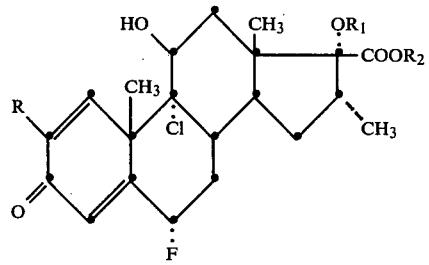

wherein R is hydrogen or chlorine, $R_1$ is the acyl radical of a lower aliphatic carboxylic acid having not more than 7 carbon atoms and $R_2$ is the moiety of an aliphatic alcohol with not more than 10 carbon atoms, which is unsubstituted or substituted by halogen, hydroxy, lower alkoxy or acyloxy containing said acyl radical $R_1$.

16. Compounds according to claim 15, wherein R is hydrogen, $R_1$ is lower alkanoyl and $R_2$ is lower alkyl.

* * * * *